United States Patent [19]
Coles et al.

[11] Patent Number: 5,513,628
[45] Date of Patent: May 7, 1996

[54] APPARATUS AND METHOD FOR VENTILATING AND ASPIRATING

[75] Inventors: Peter W. H. Coles; Randall D. Block, both of Salt Lake City; Paul A. Schumann, Centerville; James L. Sorenson, Salt Lake City, all of Utah

[73] Assignee: Sorenson Critical Care, Inc., Salt Lake City, Utah

[21] Appl. No.: 91,324

[22] Filed: Jul. 14, 1993

[51] Int. Cl.$^6$ ................................................. A61M 16/00
[52] U.S. Cl. ................ 128/200.26; 128/207.14; 128/207.16
[58] Field of Search .................. 128/200.26, 207.14, 128/207.15, 207.16; 604/53, 163, 164, 171

[56] References Cited

U.S. PATENT DOCUMENTS

| | | | |
|---|---|---|---|
| 3,991,762 | 11/1976 | Radford | 128/200.26 |
| 4,327,723 | 5/1982 | Frankhouser | 604/53 |
| 4,351,328 | 9/1982 | Bodai | 128/207.14 |
| 4,569,344 | 2/1986 | Palmer | 128/207.16 |
| 4,638,539 | 1/1987 | Palmer | 128/207.16 |
| 4,696,296 | 9/1987 | Palmer | 128/207.16 |
| 4,805,611 | 2/1989 | Hodgkins | 128/207.14 |
| 4,825,859 | 5/1989 | Lambert | 128/202.16 |
| 4,834,726 | 5/1989 | Lambert | 128/200.26 |
| 4,836,199 | 6/1989 | Palmer | 128/207.16 |
| 4,838,255 | 6/1989 | Lambert | 128/202.16 |
| 4,872,579 | 10/1989 | Palmer | 128/207.16 |
| 4,938,741 | 7/1990 | Lambert | 604/19 |
| 4,967,743 | 11/1990 | Lambert | 128/207.16 |
| 4,981,466 | 1/1991 | Lambert | 604/19 |
| 5,025,806 | 6/1991 | Palmer et al. | 128/207.14 |
| 5,029,580 | 7/1991 | Radford et al. | 128/207.14 |
| 5,065,754 | 11/1991 | Jensen | 128/200.26 |
| 5,083,561 | 5/1992 | Russo | 128/207.16 |
| 5,107,829 | 4/1992 | Lambert | 128/207.14 |
| 5,133,345 | 7/1992 | Lambert | 128/207.14 |
| 5,158,569 | 10/1992 | Strickland et al. | 128/207.14 |
| 5,309,902 | 5/1994 | Kee et al. | 604/171 |
| 5,325,850 | 7/1994 | Ulrich et al. | 128/207.16 |
| 5,333,606 | 8/1994 | Schneider et al. | 604/171 |
| 5,333,607 | 8/1994 | Kee et al. | 604/171 |

*Primary Examiner*—Aaron J. Lewis
*Attorney, Agent, or Firm*—Trask, Britt & Rossa

[57] ABSTRACT

A sealed ventilation circuit adapter that enables simultaneous patient ventilation and safe tracheal suctioning is embodied to accommodate any of a wide variety of commercially available suction catheters. The adapter comprises a manifold assembly, and a catheter carrier. The manifold assembly may be attached to a patient for an extended period, while the catheter carrier is advantageously constructed as a single procedural use disposable device. The carrier couples with the manifold assembly and functions to effect an introduction of a catheter through a normally closed valve structure carried by the manifold assembly.

58 Claims, 5 Drawing Sheets

APPARATUS AND METHOD FOR VENTILATING AND ASPIRATING

BACKGROUND OF THE INVENTION

1. Field

This invention relates to means for ventilating and aspirating the respiratory tracts of medical patients. It is particularly directed to an improved ventilation circuit adapter.

2. State of the Art

Currently available means for ventilating and aspirating congested lungs and obstructed breathing passage ways may be classified as either "simple" or "complex." Devices of both classes have significant drawbacks and limitations. The available devices of simple construction tend to expose both the patient and the service provider to microbial contaminants. Although these devices are relatively less expensive, their use potentially provides dangerously inadequate patient ventilation during the aspirating procedure. More elaborate devices tend to be physically obstructive and economically prohibitive to use.

In common medical practice, a medical practitioner inserts a tracheal suctioning catheter into a medical patient's lungs. The catheter may be positioned within a tracheal tube, endotracheal tube or nasopharyngeal tube intubated at a tracheotomy incision, mouth or nasal opening, respectively. The end of the catheter accessible by the medical practitioner is regarded as its "proximal" end. The end of the catheter remote from the practitioner, that is, within the patient, is regarded as its "distal" end. In a typical procedure, negative pressure is exerted at the proximal end of the catheter. Undesired respiratory fluids and mucoid secretions are thereby evacuated from the medical patient through the distal end of the catheter.

In a relatively simple practice, a source of vacuum pressure remains attached to the proximal catheter end. Negative pressure is not communicated to the distal catheter end initially. Rather, negative pressure is communicated to an aperture near the proximal catheter end. When aspiration of the patient is desired, the practitioner plugs the aperture, normally with a finger or thumb. Negative pressure is thereby instantaneously diverted from the small aperture near the proximal catheter end through the catheter lumen to the distal end of the catheter. In this fashion, undesired respiratory fluids are aspirated from the respiratory tract of the patient. The suctioning catheter is then disconnected from the vacuum source and discarded after a single use.

Ventilation of the patient simultaneously with this aspirating procedure is generally impractical. Such ventilation inherently requires assistance from additional personnel as well as mechanical assistance, neither of which is available as a matter of course. Accordingly, the aspirating procedure must ordinarily be completed within a short period of time. Otherwise, the patient may experience oxygen deficiency and be exposed to the resulting potential for heart arrhythmia and/or failure.

More complex aspirating devices are available, which while avoiding some of the disadvantages attendant to the structurally more simple devices, impose additional disadvantages. For example, they are significantly more expensive to construct, and their greater number of moving parts increases the risk of disfunction during use. They are also larger and more cumbersome to use, imposing a greater physical interference with other, related procedures.

The complex, closed-system devices are characteristically comprised of a manifold structure enabling introduction of ventilating gases and intermittent exhalation of patient breath simultaneously with insertion and operation of the tracheal suctioning catheter. These systems almost universally involve at least one collapsible, plastic envelope entirely surrounding the catheter and purporting to provide a sterile barrier between the otherwise exposed external surface of the catheter and the ambient atmosphere. In practice, a practitioner manually externally collapses the envelope onto the external surface of the catheter and advances the catheter into the throat of a patient, retracting the catheter in a similar fashion following the aspiration procedure.

These closed-system devices under present medical protocol are ordinarily used at least hourly for up to 48 hours for each patient before being replaced. Problems attendant to such frequent and repeated in-dwelling use are numerous, among other problems constriction of the catheter lumen and valve flow path with dried and drying phlegm and other respiratory secretions, creation of contaminant-allowing pinholes in the collapsible plastic barrier and the need to physically move the lengthy and cumbersome devices from one location on the body of the patient to another when the devices interfere with other procedures. Associated with the dried and drying secretions inside the lumen are like secretions on the exterior of the catheter wall which accumulate at the manifold wiper seal; such thick and undesired respiratory secretions not only restrict the facile movement of the catheter through the manifold, but also can be unavoidably reintroduced to the patient in subsequent repeat procedures.

Material prior art structures and methods are described among other places in U.S. Pat. Nos. 5,133,345 to Lambert; 5,107,829 to Lambert; 5,083,561 to Russo; 5,065,754 to Jensen; 5,029,580 to Radford et al.; 5,025,806 to Palmer et al.; 4,981,466 to Lambert; 4,967,743 to Lambert; 4,938,741 to Lambert; 4,872,579 to Palmer; 4,838,255 to Lambert; 4,836,199 to Palmer; 4,834,726 to Lambert; 4,825,859 to Lambert; 4,805,611 to Hodgkins; 4,696,296 to Palmer; 4,638,539 to Palmer; 4,569,344 to Palmer; 4,327,723 to Frankhouser; and 3,991,762 to Radford.

Other closed-system, sterility preserving devices which involve sterile barriers formed of rubber-like materials and intended for penetration by rigid cannulae include: rubber like caps fitted on "y" injection site structures and located at the end of indwelling intravenous catheters, such as those distributed by HARMAC Medical Specialties, Inc. of Buffalo, N.Y. under the product number H1429104; rubber-like caps fitted on housing structure anchorable at injection sites, such as those distributed by Baxter Healthcare Corp. of Deerfield, Ill. under product number 2N3399 and their trademark "InterLink™;" and threaded lock cannula used in conjunction with the Baxter InterLink™ for needleless injection by Becton Dickinson & Co. of Franklin Lakes, N.J. under product number 303369 and their trademark "Inter-Link™."

U.S. Pat. No. 4,351,328 to Bodai discloses a method and apparatus for accomplishing endotracheal suctioning of a patient without the need for disconnecting the patient from a respirator. The disclosed apparatus permits the maintenance of positive end expiratory pressure without interruptions during suctioning. A notable feature of the device is the ease with which a suctioning tube may be removed from an associated ventilation manifold.

There remains a need for a ventilating and aspirating device, wherein a closed-system, multiple use manifold for a single patient is coupled with a single-patient, single use catheter, which structure is comprised of relatively few parts, is easily assembled and is not susceptible to disfunction.

Also, a need remains for a tracheal suctioning device which unobtrusively enables ongoing closed-system ventilation and repeated aspiration of a single patient without interim obstruction of peripheral procedures.

SUMMARY OF THE INVENTION

The present invention provides an improved apparatus and method for simultaneously ventilating and aspirating a medical patient. It may be embodied as a sealed ventilation circuit adapter that enables simultaneous patient ventilation and safe tracheal suctioning.

The adapter of this invention may be embodied to accommodate any of a wide variety of commercially available suction catheters. Catheters with flared tips, obvious depth markings, and normally closed vacuum control valves are presently considered to be most useful. Currently preferred embodiments of the adapter comprise two primary components: a manifold assembly, and a catheter carrier. The manifold assembly will ordinarily be attached to a patient for an extended period, typically 24–48 hours. The catheter carrier is advantageously constructed as a single procedural use disposable device; it is ideally constructed to accept interchangeably a variety of commercially available catheters.

The invention enables a practitioner to insert a flexible catheter tube into either lung of a patient in one smooth motion without risk of contamination or infection and without assistance from others. Additionally, a practitioner is able to activate vacuum pressure with either hand and without assistance from others.

A standard flexible tracheal suctioning catheter tube is attached at the proximal (practitioner) end to a fitting cylinder for insertion into a vacuum source. The cylinder includes an offset opening which when plugged transfers communication of the vacuum pressure from outside the catheter to the internal lumen of the catheter. The distal (patient) end of the catheter tube is structured to permit respiratory secretions to be suctioned into the lumen of the catheter tube.

The catheter tube is slidable lengthwise through a passageway in a multi-function manifold positioned at the distal end of the apparatus. The manifold preferably includes a port at the distal end for attachment to and communication with an indwelling intubation device, such as a tracheal tube, endotracheal tube or nasopharyngeal tube. The manifold also preferably includes a ventilating structure extending radially from and in fluid communication with the passageway, for selectively introducing ambient air, oxygenated air and other therapeutic gasses into the respiratory system of the patient. Other conduits may also be provided for the introduction of other suitable gases and lavage solutions to the respiratory system.

Specifically, this invention provides an advantageous ventilation circuit adapter for interfacing a suction catheter with an intubation device. The adapter may be visualized as comprising two major components; specifically, a manifold assembly and a catheter carrier. In practice, the adaptor may be associated in a package or kit with one or more catheters. Alternatively, a manifold assembly may be associated with a plurality of catheter carriers.

The manifold generally has a body with an open interior. A distal end portion of the body is adapted to couple with an intubation device. A proximal end portion of the body is formed as an open port defined by a continuous wall. The manifold may take various forms, but its proximal end portion should be approximately axially aligned with its distal end portion so that a catheter may be inserted through the proximal end portion to exit from the distal end portion. A directional barrier is carried by the proximal end portion of the manifold assembly. It is constructed and arranged to effect a seal against fluid flow through the open interior of the manifold towards the proximal end portion but to pass a catheter introduced through the proximal end portion.

Preferably, the directional barrier is configured to be inserted in the proximal end portion in sealing relationship with the open interior, and comprises a normally closed valving structure. The normally closed valve structure may be constructed and arranged to effect a sliding seal arrangement with the external surface of a catheter passed through the body of the manifold; that is, from the proximal end portion towards the distal end portion through the valve structure. Preferably, the valve and catheter carrier are mutually adapted to effect this sliding seal. The valve structure may carry detection means constructed and arranged to signal the precise location of the tip of a catheter positioned within the valve structure. For example, these means may signal, by resistance to travel or sound, the presence of the tip when it is moved to the proximity of the valve structure from a location closer to the distal end portion of the manifold assembly.

The manifold assembly desirably includes a ventilation port in fluid flow communication with the open interior of the manifold body. The central axis of the ventilation port will ordinarily be oriented transverse the central axes of the proximal end portion and the distal end portion of the manifold. A lavage port may also be provided in fluid flow communication with the open interior. The central axis of the lavage port should also be oriented transverse the central axes of the proximal end portion and the distal end portion.

The catheter carrier typically includes a leading end portion adapted to couple with the proximal end portion of the manifold and a trailing end portion carrying a catheter introducer structure. The introducer structure is constructed and arranged to interface with the directional barrier when the leading end portion of the carrier is coupled with the proximal end portion of the manifold. For example, it may comprise an introducer tip constructed as a continuous wall to define an interior passageway configured to receive and pass a catheter and an exterior surface configured to interface with the directional barrier. The directional barrier is further preferably structured to effect a resilient seal against an internal surface of the continuous wall. The interior passageway may include an entry constructed and arranged to effect a sliding seal with the exterior surface of a catheter. In any event, the exterior surface of the introducer tip and the directional barrier are mutually adapted to effect a sealed relationship when the leading end portion of the catheter carrier is coupled with the proximal end portion of the manifold body.

The directional barrier may be structured to effect a resilient seal both against an internal surface of the open interior of the manifold body and between the proximal end portion of the body and the catheter carrier.

A fluid collector may be carried by the trailing end portion of the catheter carrier. This collector functions to accumulate sputum fluids and the like wiped from a catheter as it is withdrawn through the barrier seal. In one embodiment, the collector includes a chamber positioned in approximate axial alignment with the distal end portion opposite the manifold with respect to the leading end portion. A proximal closing member for the chamber carries an entry approximately axially aligned with the introducer tip. The closing member may be structured to effect a sliding seal with the exterior surface of a catheter.

The chamber is desirably structured as a hollow cylindrical extension from the trailing end portion of the carrier. The closing member is desirably structured as an end panel of the extension with a central opening adapted to receive a catheter in friction-slipping engagement. The term "friction slipping," as used in this disclosure, refers to a slidable association in which the exterior surface of the catheter is engaged about its circumference by the interior surface of the central opening of the end panel. Fluids adhering to the catheter are thus removed by a wiping action as the catheter is withdrawn through the opening. The end panel conveniently comprises a removable cap structured and arranged to effect a sealed closure of the cylindrical extension.

In use, the manifold assembly is interposed between a patient's indwelling tube at the distal end of the manifold and a ventilating circuit. These junctions preferably embody a swivel configuration to permit left or right bedside placement of the ventilation circuitry, and free rotation of the ventilation circuit with patient head movement to reduce the risk of extubation.

The directional barrier may be configured as an elongate pressure and sterility barrier, and the normally closed valve may be in the shape of a duckbill, with a normally closed central aperture interposed within the passageway of the manifold. Whether the barrier is structured to include an aperture of elongate transverse dimension or a simple slit in a membranous end of the barrier wall, the barrier in combination with the adapter assembly provides an effective seal against patient expectoration, contaminant migration and pressure leakage.

The catheter carrier may be configured as an adapter assembly surrounding the catheter, including an introducer tip and a concentric outer introducer housing connected at one end by an adapter base. The introducer housing fits snugly over the outside of the proximal end of the manifold. As the introducer housing is slid over the manifold, first coupling structure carried by the external surface of the manifold engages second coupling structure associated with the internal wall of the introducer housing. The first and second coupling structures are mutually adapted to allow the practitioner to slide the adapter assembly and manifold toward one another until the manifold is seated against the adapter base. Then the housing is rotated with respect to the adapter to positively lock the adapter and manifold together during use of the device.

The introducer housing may be slid over the proximal end of the manifold. An initial sterile barrier is thereby created. After the initial barrier is created, the introducer housing is further slid toward the manifold, causing the introducer tip to penetrate the aperture of the directional barrier. Though this penetration may preliminarily partially compromise the aperture seal, the initial sterile barrier between the manifold and adapter maintains a closed-system environment within the manifold. After the introducer tip has penetrated the directional barrier, the catheter can be advanced, with minimal frictional resistance, through the manifold and indwelling tube into either lung of the patient.

Once the catheter and adapter are attached to the manifold, a presuction saline lavage is typically introduced through the lavage port in the manifold which directs the respiratory secretion flow into the patient tube through the distal end of the manifold. The lavage port is purposefully located immediately adjacent to the patient tube and with a non-perpendicular fluid injection angle so as to optimally direct the saline flow into the patient tube with little risk of back flow into the ventilation circuit. One preferred manifold design incorporates a window through which a practitioner may view the catheter, its suctioned contents and any depth markings which may be printed on the catheter.

While the practitioner is performing the evacuation procedure, the catheter may be repeatedly inserted and retracted with selective introduction of lavage fluid through a lavage port on the manifold. The manifold is configured to prevent lavage fluid from draining through the ventilation port, obviating the need for the manifold to be tilted during lavage and thereby averting the potential for disconnection of the manifold from the indwelling endotracheal tube.

Upon repeated advancement and retraction of the catheter during an evacuation procedure, undesired respiratory secretions are prevented from flowing into the ventilation port or back toward the patient. Such secretions are squeegeed off of the external surface of the catheter during retraction.

The squeegee function is accomplished by a wiper seal snugly surrounding the catheter within the proximal end of the adapter assembly. The wiper seal has two primary functions: to clean the external catheter wall during retraction so as to minimize practitioner exposure to patient contaminants; and to maintain a pressure seal around the catheter, ensuring a continuous closed, leak tight ventilation circuit. The preferred wiper seal configuration interfaces with the catheter tube with low frictional resistance, facilitating facile catheter insertion.

A sputum collector compartment is located between the wiper seal and the base of the adapter to accumulate the undesired secretions. The sputum collector or trap has two primary functions. It traps the wiper seal between the wiper trap and the adapter housing, and acts as a catheter guide during insertion and retraction of the catheter.

Upon completion of an evacuation procedure, a practitioner retracts the catheter. In some arrangements, a structure, such as a flare at the distal tip of the catheter, catches against a trap wall narrowing in the catheter passageway within the introducer tip. This flare to trap wall contact further enhances and maintains the closed-system environment within the manifold by providing a positive stop which prevents a practitioner from inadvertently retracting a catheter from the manifold and catheter adapter.

After the practitioner has performed the respiratory evacuation procedure, the introducer housing may be axially rotated in the direction opposite to the direction it was turned at the beginning of the procedure, thereby to decouple the adapter assembly so that it can be retracted from the manifold.

As the adapter assembly is being retracted from the manifold, the introducer housing maintains a closed-system seal, even as the introducer tip within is pulled through the directional barrier. After the aperture in the directional barrier is closed, thereby maintaining a pressure and sterility barrier, the introducer housing is retracted proximally off from the manifold. The single use catheter and adapter assembly may then be dropped onto the sterile field barrier atop the patient, together with the surgical gloves, and the sterile field may be wrapped around the gloves, catheter and adapter assembly and discarded appropriately, leaving the closed-system, single-patient manifold in place for later multiple uses.

A dust cap, typically tethered to the manifold, may be placed over the proximal end of the manifold between suction procedures. The dust cap acts as a protective sterile barrier between the suction procedures as well as a seal against pressure differentials across the manifold to prevent back flow through the normally closed directional barrier.

It is significant that throughout the entirety of a respiratory evacuation procedures, a sterile, closed-system environment is maintained within the manifold. This invention thus makes it possible for such respiratory evacuation procedures to be accomplished without the need for ancillary personnel assistance. An individual respiratory nurse or technician can perform the entire procedure.

Further, it is significant that this invention provides means whereby throughout the entirety of such procedures, ongoing oxygenation or other ventilation of the patient can be maintained, without the need for repeated disconnection, connection or other moving of ventilating tubes and other auxiliary equipment.

It is also significant that the manifold, comprising the more costly portion of the adapter of this invention, unobtrusively remains attached to the patient and is reusable for numerous additional suctioning procedures with single-use catheter and carrier assemblies of relatively negligible expense.

BRIEF DESCRIPTION OF THE ILLUSTRATED DRAWINGS

In the drawings, which illustrate what is currently regarded as the best mode for carrying out the invention.

DETAILED DESCRIPTION OF THE PREFERRED EMBODIMENT

FIGS. 1–4, illustrate one configuration of a device, designated generally 100, embodying the invention. A manifold assembly, designated generally 105, comprises a body 110 with a distal end 115 and a proximal end 120. The body 110 defines a space 125 between the distal end 115 and proximal end 120. A lavage port 130 located on the body 110 of the manifold assembly 105 opens into and is in communication with the manifold space 125. Similarly, a ventilation port 135 located on the body 110 is in communication with the manifold space 125. Located at the distal end 115 of the body 110 is an endotracheal port 140 opening toward the patient and attachable to an indwelling fixture (not shown), such as a tracheal, endotracheal or nasopharyngeal tube.

Figure 1:
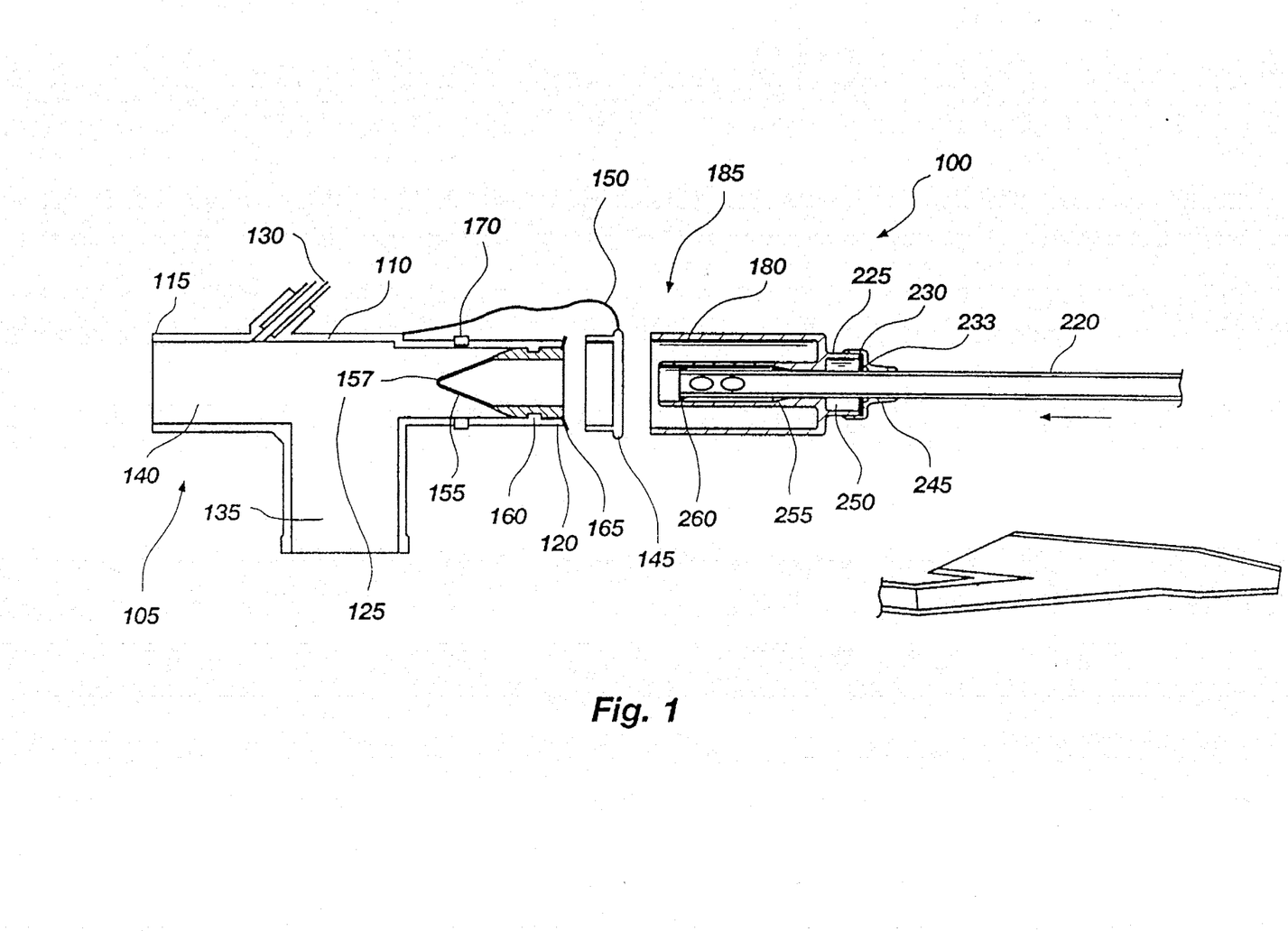
FIG. 1 is a partially exploded and partially broken away cross-sectional view in elevation of a preferred embodiment of the invention in disassembled condition.
Figure 2:
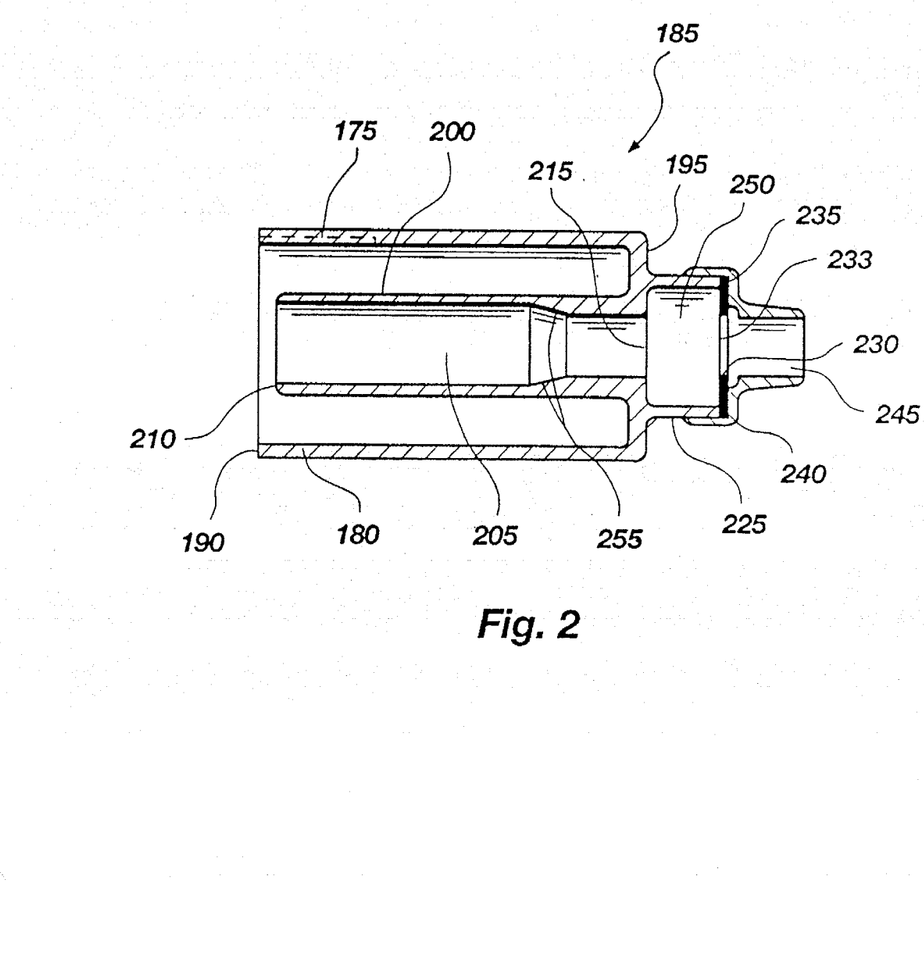
FIG. 2 is an enlargement of a portion of FIG. 1.
Figure 3:
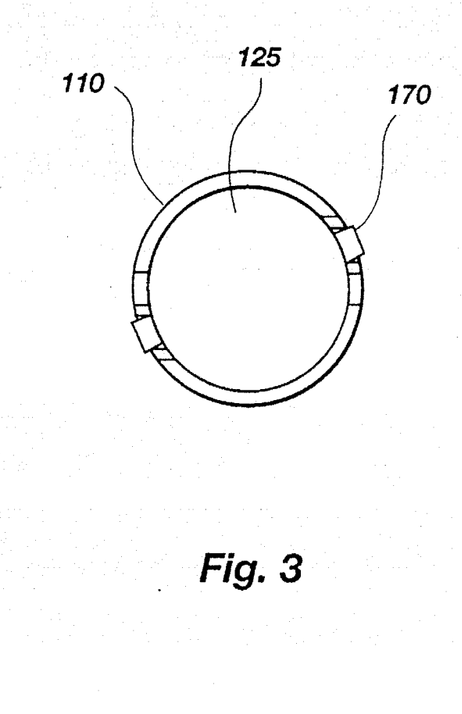
FIG. 3 is a view in elevation taken on the reference line 3—3 of FIG. 2.

A cap 145, capable of covering the proximal end 120 of the body 110, may be attached to the body 110 with a tether 150. Situated within the space 125 of the body 110 is a directional barrier 155 preferably formed of a pliant, durable, rubber-like material with strong dimensional memory. The directional barrier 155 includes a central aperture 157. The directional barrier 155 is seated around its entire cross-sectional periphery against a rim 160 extending inwardly from the internal wall of the body 110. The barrier 155 and the rim 160 interface in a manner that achieves a sealing and anchoring of the directional barrier 155 relative to the body 110. A seal extension 165 may protrude slightly from the directional barrier 155 axially beyond the proximal end 120 of the body 110 to provide additional sealing effect between the cap 145 and the body 110 when the cap 145 is in position to cover the proximal end 120 of the body 110.

At least one positioning and locking post 170 extends radially outward from the body 110 of the manifold assembly 105. The post 170 interacts with a locking channel 175 formed in the internal wall of the introducer housing 180 of a catheter adapter 185, as illustrated more clearly in FIG. 2. The channel 175 extends axially from the adapter front 190 in the direction of the adapter base 195, providing relative positioning of the manifold assembly 105 and the catheter adapter 185. The channel 175 then continues circumferentially at approximately a right angle from the axially directed channel 175, providing a means of locking the manifold assembly 105 and the catheter adapter 185 together when the post 170 has been moved axially and then radially within the channel 175. The seal extension 165 is shown configured to seal against the internal wall of the introducer housing 180 as the catheter adapter 185 and manifold assembly 105 are in the process of being assembled. The seal extension 165 is further structured to seal against the adapter base 195 when the catheter adapter 185 is locked to manifold assembly 105. In this attached position, the resilience of the seal extension 165 biases the adapter 185 axially to maintain locking pressure between the locking post 170 of the manifold assembly 105 and the channel 175 of the introducer housing 180.

The catheter adapter 185 comprises an introducer tip 200 situated concentric with and inside of the introducer housing 180. The introducer tip 200 is seated against, and may be formed integrally with the adapter base 195. A catheter passageway 205 is formed through the length of the introducer tip 200, opening at the leading edge 210 and through a catheter opening 215 in the adapter base 195. The catheter opening 215 may be formed with a cross-sectional dimension slightly larger than but corresponding to the outside cross-sectional dimension of a tracheal suctioning catheter 220.

Trap walls 225 extend axially from, and are formed integrally with, the adapter base 195. A pliant and resilient washer-like wiper seal 230 with a hole 233 therethrough is placed against the distal edge 235 of the trap walls 225. A trap cap 240 is attached to the trap walls 225 and holds the wiper seal 230 in place. The trap cap 240 includes a support opening 245 which provides catheter guidance and relief of strain on the catheter 220 imposed by non-axial forces encountered during insertion and retraction of the catheter 220. In combination, the wiper seal 230, the trap cap 240 and the trap wall 225 contribute to the sterility and pressure barrier function of the manifold 185 during use. The trap walls 225, together with the wiper seal 230 and the trap cap 240, define a sputum collector 250.

Upon retraction of the catheter 220, sputum, phlegm and other undesired respiratory secretions are squeegeed from the external surface of the catheter 220 by the wiper seal 230. The diameter of the hole 233 is desirably sized slightly smaller than the outer diameter of the catheter 220 to facilitate this function. These undesired respiratory liquids are then directed into the sputum collector 250 where they are retained from leakage back toward the patient or out toward the respiratory practitioner. With the practitioner being equipped with protective hand ware and the patient being covered by a sterile field barrier under the retracted catheter 220, adequate protection from cross-contamination is thereby achieved.

Figure 6:
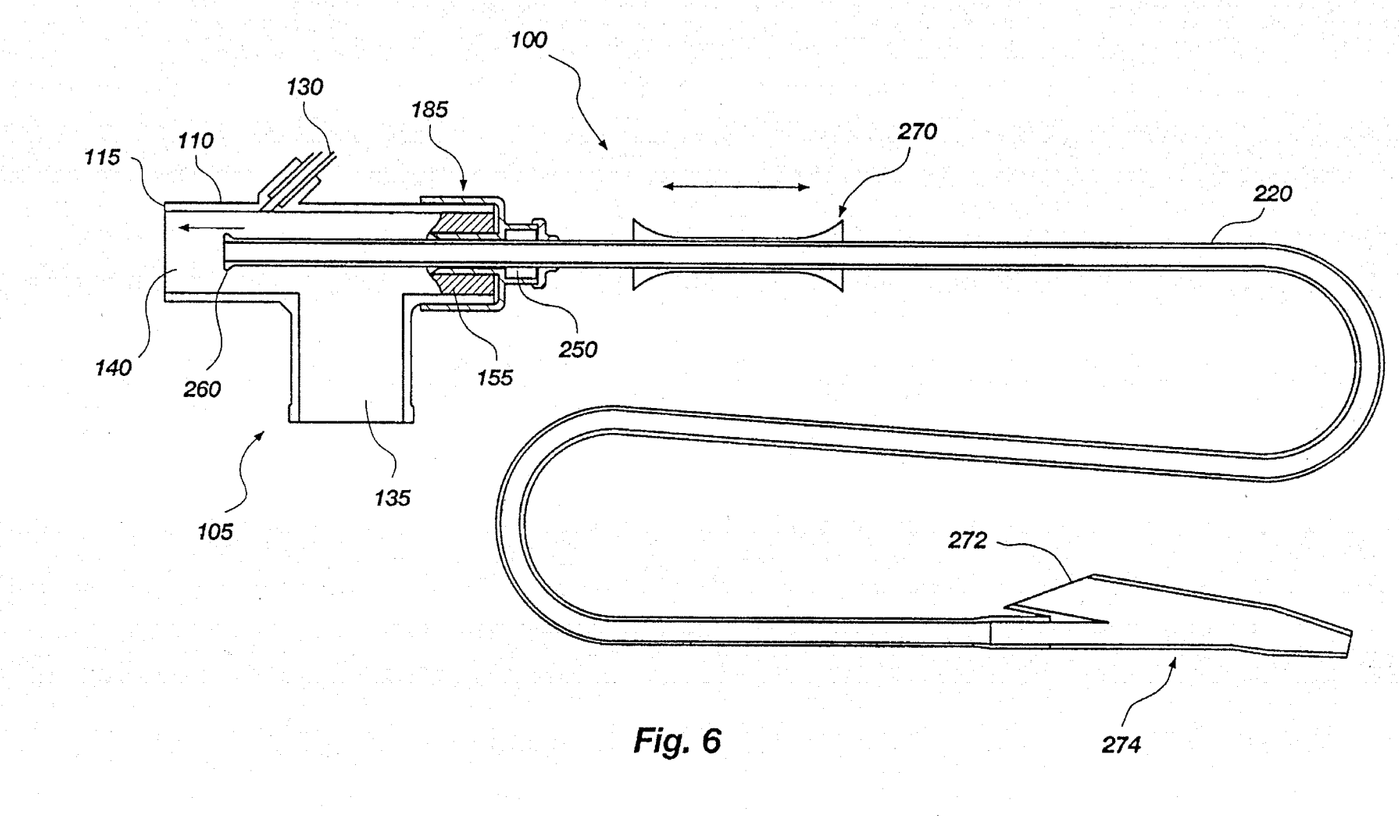
FIG. 6 is a view similar to FIG. 5, showing the components in assembled condition.

The catheter passageway 205 narrows at a reducing constrictor 255 near the catheter opening 215. A flare 260 at the catheter nozzle 265 catches against the reducing constrictor 255 upon retraction of the catheter 220. The embodiment illustrated by FIG. 6 provides a catheter advancer 270. A practitioner can press the walls of the advancer 270 down upon a catheter 220 for selectively advancing and retracting the catheter 220. In this fashion, the practitioner can manipulate the catheter without touching it and without the need for special hand ware.

Figure 4:
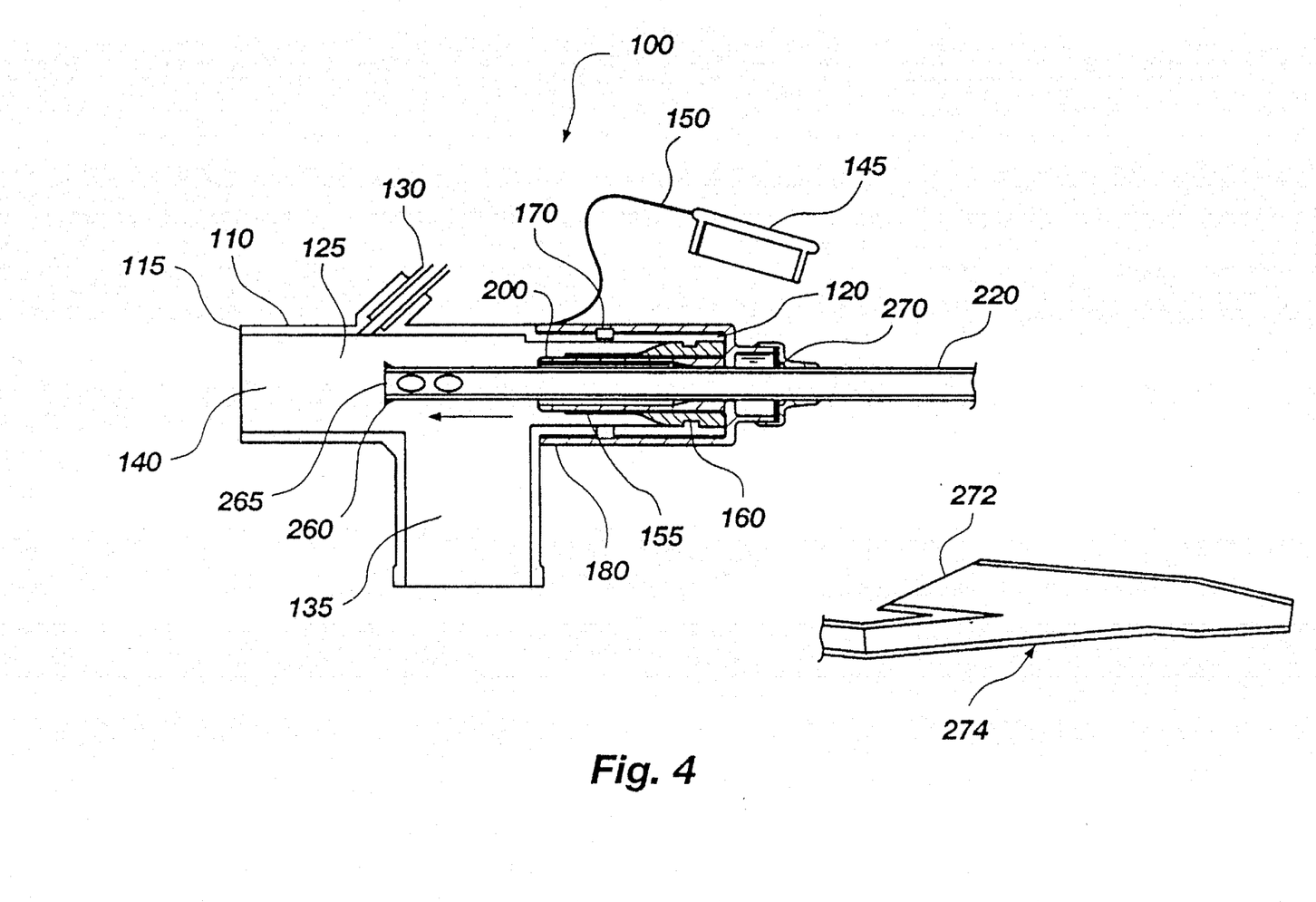
FIG. 4 is a view similar to FIG. 1, but showing the components in assembled condition.
Figure 5:
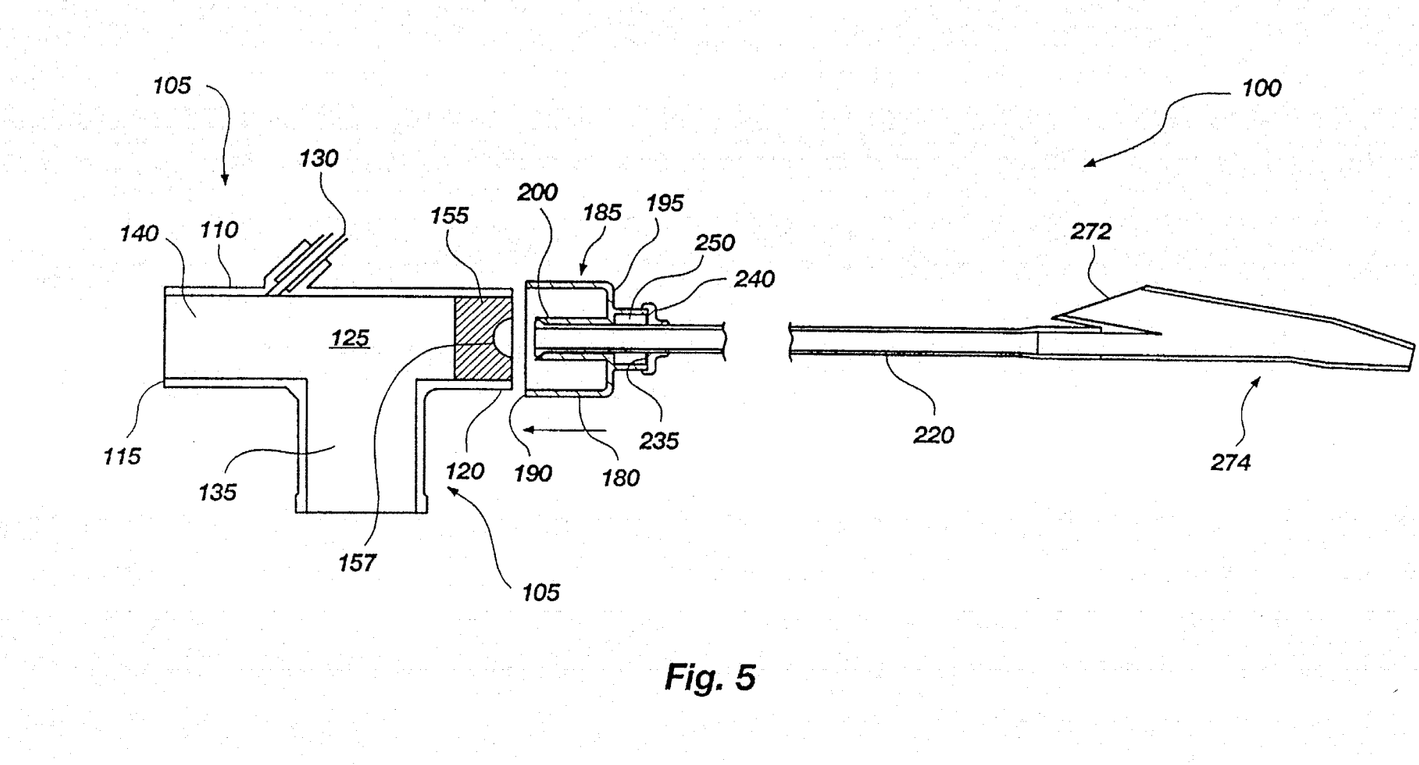
FIG. 5 is a partially exploded and partially broken away cross-sectional view similar to FIG. 1 of an alternative embodiment of the invention.

As best shown by FIGS. 4 and 6, the device 100 and its respective components allow a respiratory practitioner to maintain a closed-system within the single-patient, multiple use manifold assembly 105 throughout attachment of the catheter adapter 185 to the manifold assembly 105, evacuation of a medical patient through ambidextrous actuation of the vacuum pressure by selectively plugging an opening 272 in an actuator cylinder 274, retraction of the tracheal catheter 220 and detachment of the single-use, disposable catheter adapter 185. The practitioner may then, with minimal waste and cost, discard the catheter 220 and adapter structure 185 and place the cap 145 over the proximal end 120 of the manifold assembly 105 until next use, leaving no partially obstructed catheter, plastic envelope and complicated valve structure to interfere with other procedures and auxiliary equipment.

The present invention may be embodied in other specific forms without departing from its spirit or essential characteristics. Further objects and advantages of this invention will become apparent from a consideration of the drawings and ensuing description of it. The described embodiments are to be considered in all respects only as illustrative, and not restrictive. The scope of the invention is, therefore, indicated by the appended claims, rather than by the foregoing description. All changes which come within the meaning and range of equivalency of the claims are to be embraced within their scope.

What is claimed is:

1. A ventilation circuit adapter for interfacing a suction catheter with an intubation device, comprising:
    a manifold assembly, having:
        a body with an open interior;
        a distal end portion of said body being adapted to couple with said intubation device,
        a proximal end portion of said body being formed as an open port defined by a continuous wall, said proximal end portion being approximately axially aligned with said distal end portion so that a catheter may be inserted through said proximal end portion to exit from said distal end portion;
    a directional barrier carried by said proximal end portion, constructed and arranged to effect a seal against fluid flow through said open interior towards said proximal end portion but to pass a said catheter introduced through said proximal end portion, said directional barrier carrying detection means constructed and arranged to signal the presence of the tip of a catheter when said tip is moved to the proximity of said directional barrier from a location closer to said distal end portion; and
    structural means for associating a catheter with said proximal end, said structural means being releasably connectable to said proximal end portion.

2. An adapter according to claim 1, wherein said manifold assembly includes a ventilation port in fluid flow communication with said open interior, said ventilation port having a central axis transverse the central axes of said proximal end portion and said distal end portion.

3. An adapter according to claim 2, wherein said manifold assembly includes a lavage port in fluid flow communication with said open interior, said lavage port having a central axis transverse said central axes of said proximal end portion and said distal end portion.

4. An adapter according to claim 1, wherein said directional barrier is configured to be inserted in said proximal end portion in sealing relationship with said open interior and comprises a normally closed valving structure.

5. An adapter according to claim 4, wherein said normally closed valve structure is constructed and arranged to effect a sliding seal with the external surface of a catheter as a said catheter is passed from said proximal end portion towards said distal end portion though said valve structure.

6. An adapter according to claim 4, wherein said directional barrier is structured to effect a resilient seal against an internal surface of said continuous wall of said proximal end portion.

7. An adapter according to claim 6, wherein said manifold assembly includes a ventilation port in fluid flow communication with said open interior, said ventilation port having a central axis transverse the central axes of said proximal end portion and said distal end portion.

8. An adapter according to claim 7, wherein said manifold assembly includes a lavage port in fluid flow communication with said open interior, said lavage port having a central axis transverse said central axes of said proximal end portion and said distal end portion.

9. An adapter according to claim 1, wherein said structural means comprises:
    a catheter carrier, including:
        a leading end portion adapted to couple with said proximal end portion; and
        a trailing end portion carrying a catheter introducer structure, said introducer structure being constructed and arranged to interface with said directional barrier when said leading end portion is coupled with said proximal end portion.

10. An adapter according to claim 9, wherein said introducer structure comprises:
    an introducer tip constructed as a continuous wall to define:
        an interior passageway configured to receive and pass a catheter; and
        an exterior surface configured to interface with said directional barrier.

11. An adapter according to claim 10 wherein said interior passageway is constructed and arranged to effect a sliding seal with the exterior surface of a catheter.

12. An adapter according to claim 10, wherein said exterior surface of said introducer tip and said directional barrier are mutually adapted to effect a sealed relationship when said leading end portion is coupled with said proximal end portion.

13. An adapter according to claim 9, wherein said directional barrier is configured to be inserted in said proximal end portion in sealing relationship with said open interior and comprises a normally closed valving structure.

14. An adapter according to claim 13, wherein said introducer structure comprises:
    an introducer tip constructed as a continuous wall to define:

an interior passageway configured to receive and pass a catheter; and an exterior surface configured to interface with said directional barrier.

15. An adapter according to claim 14, wherein said interior passageway includes an entry which is constructed and arranged to effect a sliding seal with the exterior surface of a catheter.

16. An adapter according to claim 14, wherein said exterior surface of said introducer tip and said directional barrier are mutually adapted to effect a sealed relationship when said leading end portion is coupled with said proximal end portion.

17. An adapter according to claim 16, wherein said directional barrier is structured to effect a resilient seal against an internal surface of said continuous wall of said proximal end portion and between said proximal end portion and said catheter carrier.

18. An adapter according to claim 17, wherein said normally closed valve structure is constructed and arranged to effect a sliding seal with the external surface of a catheter as a said catheter is passed from said proximal end portion towards said distal end portion though said valve structure.

19. An adapter according to claim 17, wherein said manifold assembly includes a ventilation port in fluid flow communication with said open interior, said ventilation port having a central axis transverse the central axes of said proximal end portion and said distal end portion.

20. An adapter according to claim 19, wherein said manifold assembly includes a lavage port in fluid flow communication with said open interior, said lavage port having a central axis transverse said central axes of said proximal end portion and said distal end portion.

21. A ventilation circuit adapter for interfacing a suction catheter with an intubation device, comprising:

a manifold assembly, having:
 a body with an open interior:
  a distal end portion of said body being adapted to couple with said intubation device,
  a proximal end portion of said body being formed as an open port defined by a continuous wall, said proximal end portion being approximately axially aligned with said distal end portion so that a catheter may be inserted through said proximal end portion to exit from said distal end portion, and
  a directional barrier carried by said proximal end portion, constructed and arranged to effect a seal against fluid flow through said open interior towards said proximal end portion but to pass a said catheter introduced through said proximal end portion; wherein said directional barrier is configured to be inserted in said proximal end portion in sealing relationship with said open interior, and comprises a normally closed valving structure which is constructed and arranged to effect a sliding seal with the external surface of a catheter as a said catheter is passed from said proximal end portion towards said distal end portion though said valve structure;
 detection means carried by said valve structure and constructed and arranged to signal the presence of the tip of a catheter positioned within said valve structure when said tip is moved to the proximity of said valve structure from a location closer to said distal end portion; and
 structural means for associating a catheter with said proximal end, said structural means being releasably connectable to said proximal end portion.

22. A ventilation circuit adapter for interfacing a suction catheter with an intubation device, comprising:

a manifold assembly, having:
 a body with an open interior;
  a distal end portion of said body being adapted to couple with said intubation device,
  a proximal end portion of said body being formed as an open port defined by a continuous wall, said proximal end portion being approximately axially aligned with said distal end portion so that a catheter may be inserted through said proximal end portion to exit from said distal end portion, and
  a directional barrier carried by said proximal end portion, constructed and arranged to effect a resilient seal against an internal surface of said continuous wall of said proximal end portion and between said proximal end portion and a catheter carrier against fluid flow through said open interior towards said proximal end portion but to pass a said catheter introduced through said proximal end portion, wherein said directional barrier is configured to be inserted in said proximal end portion in sealing relationship with said open interior and comprises:
   a normally closed valving structure which is constructed and arranged to effect a sliding seal with the external surface of a catheter as a said catheter is passed from said proximal end portion towards said distal end portion though said valve structure, and which carries detection means constructed and arranged to signal the presence of the tip of a catheter positioned within said valve structure when said tip is moved to the proximity of said valve structure from a location closer to said distal end portion; and
 structural means for associating a catheter with said proximal end, said structural means being releasably connectable to said proximal end portion and comprising:
  a catheter carrier, including:
   a leading end portion adapted to couple with said proximal end portion; and
   a trailing end portion carrying a catheter, introducer structure, said introducer structure being constructed and arranged to interface with said directional barrier when said leading end portion is coupled with said proximal end portion and comprising:
    an introducer tip constructed as a continuous wall to define:
     an interior passageway configured to receive and pass a catheter: and
     an exterior surface configured to interface with said directional barrier, wherein said exterior surface of said introducer tip and said directional barrier are mutually adapted to effect a sealed relationship when said leading end portion is coupled with said proximal end portion 23. A ventilation circuit adapter for interfacing a suction catheter with an intubation device, comprising:

a manifold assembly, having:
 a body with an open interior;
  a distal end portion of said body being adapted to couple with said intubation device,
  a proximal end portion of said body being formed as an open port defined by a continuous wall, said proximal end portion being approximately axially aligned with said distal end portion so that a catheter may be inserted through said proximal end portion to exit from said distal end portion, and a directional barrier carded by said proximal end portion, constructed and arranged to effect a seal against fluid flow through said open interior towards said proximal end portion but to pass a said catheter introduced through said proximal end portion: and structural means for associating a catheter with said proximal end, said structural means being releasably connectable to said proximal end portion and comprising:

a catheter carrier, including:
a leading end portion adapted to couple with said proximal end portion: and
a trailing end portion carrying a catheter introducer structure, said introducer structure being constructed and arranged to interface with said directional barrier when said leading end portion is coupled with said proximal end portion, said introducer structure comprising:
an introducer tip constructed as a continuous wall to define:
an interior passageway configured to receive and pass a catheter; and
an exterior surface configured to interface with said directional barrier; and a fluid collector carried by said trailing end portion and including:
a chamber positioned in approximate axial alignment with said distal end portion opposite said manifold with respect to said leading end portion;
a proximal closing member for said chamber with an entry approximately axially aligned with said introducer tip, said closing member being structured to effect a sliding seal with the exterior surface of a catheter.

24. An adapter according to claim 23, wherein said chamber is structured as a hollow cylindrical extension from said trailing end portion, and said closing member is structured as an end panel of said extension with a central opening adapted to receive a catheter in friction-slipping engagement.

25. An adapter according to claim 24, wherein said end panel comprises a removable cap structured and arranged to effect a sealed closure of said cylindrical extension.

26. An adapter according to claim 24, wherein said directional barrier is configured to be inserted in said proximal end portion in sealing relationship with said open interior and comprises a normally closed valving structure.

27. An adapter according to claim 26, wherein said exterior surface of said introducer tip and said directional barrier are mutually adapted to effect a sealed relationship when said leading end portion is coupled with said proximal end portion.

28. A ventilation circuit adapter for interfacing a suction catheter with an intubation device, comprising:

a manifold assembly, having:
a body with an open interior;
a distal end portion of said body being adapted to couple with said intubation device, and
a proximal end portion of said body being formed as an open port defined by a continuous wail;

a catheter carder, including:
a leading end portion adapted to couple with said proximal end portion, and
a trailing end portion carrying a catheter introducer structure; and a directional barrier carded by said proximal end portion, constructed and arranged
to effect a seal between said proximal end portion and said carrier,
to effect a seal against fluid flow through said open interior towards said proximal end portion, and
to pass a catheter introduced through said proximal end portion, said directional barrier carrying detection means constructed and arranged to signal the presence of the tip of a catheter structure when said tip is moved to the proximity of said valve structure from a location closer to said distal end portion;

said introducer structure being constructed and arranged to interface with said directional barrier when said leading end portion is coupled with said proximal end portion.

29. An adapter according to claim 28, wherein said introducer structure comprises:
an introducer tip constructed as a continuous wall to define:
an interior passageway configured to receive and pass a catheter; and
an exterior surface configured to interface with said directional barrier.

30. An adapter according to claim 29, wherein said interior passageway includes an entry which is constructed and arranged to effect a sliding seal with the exterior surface of a catheter.

31. An adapter according to claim 29, wherein said exterior surface of said introducer tip and said directional barrier are mutually adapted to effect a sealed relationship when said leading end portion is coupled with said proximal end portion.

32. An adapter according to claim 31, wherein said directional barrier is structured to effect a resilient seal against an internal surface of said continuous wall of said proximal end portion and between said proximal end portion and said catheter carrier.

33. An adapter according to claim 28, wherein said manifold assembly includes a ventilation port in fluid flow communication with said open interior, said ventilation port having a central axis transverse the central axes of said proximal end portion and said distal end portion.

34. An adapter according to claim 28, wherein said manifold assembly includes a lavage port in fluid flow communication with said open interior, said lavage port having a central axis transverse said central axes of said proximal end portion and said distal end portion.

35. An adapter according to claim 28, wherein said directional barrier comprises a normally closed valve structure constructed and arranged to effect a sliding seal with the external surface of said introducer structure.

36. A ventilation circuit adapter for interfacing a suction catheter with an intubation device, comprising:

a manifold assembly, having:
a body with an open interior;
a distal end portion of said body being adapted to couple with said intubation device, and
a proximal end portion of said body being formed as an open port defined by a continuous wall;

a catheter carrier, including:
a leading end portion adapted to couple with said proximal end portion, and
a trailing end portion carrying a catheter introducer structure; and a directional barrier carried by said proximal end portion, constructed and arranged to effect a seal between said proximal end portion and said carrier, to effect a seal against fluid flow through said open interior towards said proximal end portion, and to pass a catheter introduced through said proximal end portion;

said introducer structure being constructed and arranged to interface with said directional barrier when said leading end portion is coupled with said proximal end portion, wherein said directional barrier comprises a normally closed valve structure constructed and arranged to effect a sliding seal with the external surface of said introducer structure, and said valve structure carries detection means constructed and arranged to signal the presence of the tip of a catheter positioned within said valve structure when said tip is moved to the proximity of said valve structure from a location closer to said distal end portion.

37. A ventilation circuit adapter for interfacing a suction catheter with an intubation device, comprising:

a manifold assembly, having:
a body with an open interior;
a distal end portion of said body being adapted to couple with said intubation device,
a proximal end portion of said body being formed as an open port defined by a continuous wall:

a catheter carder, including:
a leading end portion adapted to couple with said proximal end portion, and
a trailing end portion carrying a catheter introducer structure: and a directional barrier carded by said proximal end portion, constructed and arranged
to effect a seal between said proximal end portion and said carder,
to effect a seal against fluid flow through said open interior towards said proximal end portion, and
to pass a catheter introduced through said proximal end portion;

said introducer structure being constructed and arranged to interface with said directional barrier when said leading end portion is coupled with said proximal end portion: and a fluid collector carded by said trailing end portion and including:
a chamber positioned in approximate axial alignment with said distal end portion opposite said manifold with respect to said leading end portion;
a proximal closing member for said chamber with an entry approximately axially aligned with said introducer tip, said closing member being structured to effect a sliding seal with the exterior surface of a catheter.

38. An adapter according to claim 37, wherein said chamber is structured as a hollow cylindrical extension from said trailing end portion, and said closing member is structured as an end panel of said extension with a central opening adapted to receive a catheter in friction-slipping engagement.

39. An adapter according to claim 38, wherein said end panel comprises a removable cap structured and arranged to effect a sealed closure of said cylindrical extension.

40. A ventilation circuit adapter assembly for use with an intubation device, comprising:

a manifold assembly, having:
a body with an open interior;
a distal end portion of said body being adapted to couple with said intubation device, and
a proximal end portion of said body being formed as an open port defined by a continuous wall;

a catheter carrier, including:
a leading end portion adapted to couple with said proximal end portion, and
a trailing end portion carrying a catheter introducer structure; and a directional barrier carried by said proximal end portion, constructed and arranged
to effect a seal between said proximal end portion and said carrier, and
to effect a seal against fluid flow through said open interior towards said proximal end portion;

said directional barrier carrying detection means constructed and arranged to signal the presence of the tip of a catheter structure when said tip is moved to the proximity of said valve structure from a location closer to said distal end portion;

said introducer structure being constructed and arranged to interface with said directional barrier when said leading end portion is coupled with said proximal end portion; and a catheter positioned through said introducer structure, said open interior and said distal end.

41. An assembly according to claim 40, wherein said introducer structure comprises:

an introducer tip constructed as a continuous wall to define:
an interior passageway configured to receive and pass a catheter; and
an exterior surface configured to interface with said directional barrier.

42. An assembly according to claim 41, wherein said interior passageway includes an entry which is constructed and arranged to effect a sliding seal with the exterior surface of a catheter.

43. An assembly according to claim 41, wherein said exterior surface of said introducer tip and said directional barrier are mutually adapted to effect a sealed relationship when said leading end portion is coupled with said proximal end portion.

44. An assembly according to claim 43, wherein said directional barrier is structured to effect a resilient seal against an internal surface of said continuous wall of said proximal end portion and between said proximal end portion and said catheter carrier.

45. An assembly according to claim 41, wherein said manifold assembly includes a ventilation port in fluid flow communication with said open interior, said ventilation port having a central axis transverse the central axes of said proximal end portion and said distal end portion.

46. An assembly according to claim 41, wherein said manifold assembly includes a lavage port in fluid flow communication with said open interior, said lavage port having a central axis transverse said central axes of said proximal end portion and said distal end portion.

47. An assembly according to claim 41, wherein said directional barrier comprises a normally closed valve structure constructed and arranged to effect a sliding seal with the external surface of said introducer structure.

48. An assembly according to claim 40 wherein said catheter carries indicia, and said manifold body includes a transparent window portion positioned so that said indicia are viewable through said window portion as said catheter is moved parallel the axis of said manifold body.

49. An assembly according to claim 48, wherein said indicia comprise markings carried by the exterior surface of said catheter.

50. An assembly according to claim 48, wherein said manifold assembly includes a ventilation port in fluid flow communication with said open interior, said ventilation port having a central axis transverse the central axes of said proximal end portion and said distal end portion.

51. An assembly according to claim 48, wherein said manifold assembly includes a lavage port in fluid flow communication with said open interior, said lavage port having a central axis transverse said central axes of said proximal end portion and said distal end portion.

52. A ventilation circuit adapter assembly for use with an intubation device, comprising:
  a manifold assembly, having:
    a body with an open interior;
      a distal end portion of said body being adapted to couple with said intubation device, and
      a proximal end portion of said body being formed as an open port defined by a continuous wall;
  a catheter carrier, including:
    a leading end portion adapted to couple with said proximal end portion, and
    a trailing end portion carrying a catheter introducer structure, said introducer structure comprising:
      an introducer tip constructed as a continuous wall to define:
        an interior passageway configured to receive and pass a catheter; and
        an exterior surface configured to interface with said directional barrier:
  a directional barrier carried by said proximal end portion, constructed and arranged to effect
    a seal between said proximal end portion and said carrier, and
    to effect a seal against fluid flow through said open interior towards said proximal end portion, said directional barrier comprising a normally closed valve structure constructed and arranged to effect a sliding seal with the external surface of said introducer structure;
  said introducer structure being constructed and arranged to interface with said directional barrier when said leading end portion is coupled with said proximal end portion; and
  a catheter positioned through said introducer structure, said open interior and said distal end; and
  detection means carded by said valve structure, which is constructed and arranged to signal the presence of the tip of a catheter positioned within said valve structure when said tip is moved to the proximity of said valve structure from a location closer to said distal end portion and said catheter carries structure intercooperable with said detection means.

53. A ventilation circuit adapter assembly for use with an intubation device, comprising:
  a manifold assembly, having:
    a body with an open interior;
      a distal end portion of said body being adapted to couple with said intubation device, and
      a proximal end portion of said body being formed as an open port defined by a continuous wall:
  a catheter carrier, including:
    a leading end portion adapted to couple with mid proximal end portion, and
    a trailing end portion carrying a catheter introducer structure, said introducer structure comprising:
      an introducer tip constructed as a continuous wall to define:
        an interior passageway configured to receive and pass a catheter; and
        an exterior surface configured to interface with a directional barrier:
  a directional barrier carried by said proximal end portion, constructed and arranged to effect a seal between said proximal end portion and said carder, and to effect a seal against fluid flow through said open interior towards said proximal end portion;
  said introducer structure being constructed and arranged to interface, with said directional barrier when said leading end portion is coupled with said proximal end portion; and
  a catheter positioned through said introducer structure, said open interior and said distal end; and
  a fluid collector carried by said trailing end portion and including:
    a chamber positioned in approximate axial alignment with said distal end portion opposite said manifold with respect to said leading end portion;
    a proximal closing member for said chamber with an entry approximately axially aligned with said introducer tip, said closing member being structured to effect a sliding seal with the exterior surface of a catheter.

54. An assembly according to claim 53, wherein said chamber is structured as a hollow cylindrical extension from said trailing end portion, and said closing member is structured as an end panel of said extension with a central opening adapted to receive a catheter in friction-slipping engagement.

55. An assembly according to claim 54, wherein said end panel comprises a removable cap structured and arranged to effect a sealed closure of said cylindrical extension.

56. A ventilation circuit adapter assembly for use with an intubation device, comprising:
  a manifold assembly, having:
    a body with an open interior;
      a distal end portion of said body being adapted to couple with said intubation device, and
      a proximal end portion of said body being formed as an open port defined by a continuous wall;
  a catheter carder, including:
    a leading end portion adapted to couple with said proximal end portion, and
    a trailing end portion carrying a catheter introducer structure; and
  a directional barrier carried by said proximal end portion, constructed and arranged
    to effect a seal between said proximal end portion and said carder, and
    to effect a seal against fluid flow through said open interior towards said proximal end portion;
  said introducer structure being constructed and arranged to interface with said directional barrier when said leading end portion is coupled with said proximal end portion;
  a catheter positioned through said introducer structure, said open interior and said distal end, said catheter carrying indicia, and said manifold body including a transparent window portion positioned so that said indicia is viewable through said window portion as said catheter is moved parallel the axis of said manifold body; and detection means carried by said valve structure and constructed and arranged to signal the presence of the tip of a catheter positioned within said valve structure when said tip is moved to the proximity of said valve structure from a location closer to said distal end portion and said catheter carries structure intercooperable with said detection means.

57. A ventilation circuit adapter for interfacing a suction catheter with an intubation device, comprising:.

a manifold assembly, having:
 a body with an open interior;
 a distal end portion of said body being adapted to couple with said intubation device,
 a proximal end portion of said body being formed as an open port defined by a continuous wall, said proximal end portion being approximately axially aligned with said distal end portion so that a catheter may be inserted through said proximal end portion to exit from said distal end portion;
 a catheter carrier structured and arranged to associate a catheter with said proximal end, including:
  a leading end portion;
  a trailing end portion; and
 a fluid collector carded by said trailing end .portion, wherein said fluid collector comprises:
  a chamber positioned in approximate axial alignment with said distal end portion opposite said manifold with respect to said leading end portion; and
  a proximal closing member for said chamber with an entry approximately axially aligned with an introducer tip, said closing member being structured to effect a sliding seal with the exterior surface of a catheter.

58. A ventilation circuit adapter for interfacing a suction catheter with an intubation device, comprising:

a manifold assembly, having:
 a body with an open interior;
 a distal end portion of said body being adapted to couple with said intubation device,
 a proximal end portion of said body being formed as an open port defined by a continuous wall, said proximal end portion being approximately axially aligned with said distal end portion so that a catheter may be inserted through said proximal end portion to exit from said distal end portion;
 a catheter carrier structured and arranged to associate a catheter with said proximal end, including:
  a leading end portion;
  a trailing end portion; and
 valve structure configured to be inserted in said proximal end portion in sealing relationship with said open interior, said valve structure normally being closed; and detection means carried by said valve structure, said detection means constructed and arranged to signal the presence of the tip of a catheter positioned within said valve structure when said tip is moved to the proximity of said valve structure from a location closer to said distal end portion.

* * * * *